United States Patent [19]

Sunagawa et al.

[11] Patent Number: 4,536,334
[45] Date of Patent: Aug. 20, 1985

[54] PREPARATION OF β-LACTAM DERIVATIVES

[75] Inventors: Makoto Sunagawa; Haruki Matsumura, both of Osaka; Takaaki Inoue, Hyogo; Toshiyuki Hirohashi, Osaka, all of Japan

[73] Assignee: Sumitomo Chemical Company, Limited, Osaka, Japan

[21] Appl. No.: 164,396

[22] Filed: Jun. 30, 1980

[30] Foreign Application Priority Data

| Jun. 28, 1979 | [JP] | Japan | 54-82411 |
| Jul. 5, 1979 | [JP] | Japan | 54-85610 |

[51] Int. Cl.$^3$ .......................................... C07D 205/08
[52] U.S. Cl. .............................. 260/239 A; 260/330.3
[58] Field of Search ................................... 260/239 A

[56] References Cited

U.S. PATENT DOCUMENTS

| 3,799,938 | 3/1974 | Aeusler | 544/16 |
| 3,944,545 | 3/1976 | Chou | 260/239 A |
| 3,950,352 | 4/1976 | Wolfe | 260/239 A |
| 4,257,947 | 3/1981 | Gleason | 260/239 A |

FOREIGN PATENT DOCUMENTS

| 1807498 | 6/1970 | Fed. Rep. of Germany ... 260/239 A |

OTHER PUBLICATIONS

Neimann et al., Chem. Abs., 69, 59201u, (1968).
Loev et al., Chem. Abs., 69, 76855c, (1968).
Matsura et al., JCS Chem. Comm., 1976, 451.
Hanson et al., J.C. Soc. 1965, p. 7285.
Lapidot et al., Biochim. Biophys. Acta, 138, p. 241, (1967).
Huffman et al., J.A.C.S., 99, 2352, (1977).
Bose et al., Tet. Letters, 2771, (1979).
Bick et al., Aus. J. Chem., 31, 321-6, (1978).
Hruby, Chem. Abs., 85, 143436n.
Care et al., Tetrahedron, 23, 4691, (1967).
Needles, J. Org. Chem., 29, 3632, (1964).
Boyland et al., J. Chem. Soc., 3623, (1953).

*Primary Examiner*—Mark L. Berch
*Attorney, Agent, or Firm*—Sughrue, Mion, Zinn, Macpeak, and Seas

[57] ABSTRACT

A process for preparing a β-lactam derivative having a hydrogen atom on the nitrogen atom of the β-lactam ring, which comprises reacting a β-lactam derivative having a mono- or diarylmethyl group on the nitrogen atom of the β-lactam ring with an acid or ceric ammonium nitrate to cleave the bond between the nitrogen atom and the mono- or diarylmethyl group; and novel β-lactam derivatives useful as intermediates for the synthesis of pharmaceutical agents.

4 Claims, No Drawings

PREPARATION OF β-LACTAM DERIVATIVES

BACKGROUND OF THE INVENTION

1. Field of the Invention

The present invention relates to a novel process for de-monoarylmethylation or de-diarylmethylation which comprises treating a β-lactam derivative having a mono- or diarylmethyl group on the nitrogen atom of the β-lactam ring with an acid or ceric ammonium nitrate to convert the N-substituent into a hydrogen atom; to some novel substances among the starting materials used in the above process and the desired products having an antibacterial activity; to β-lactam derivatives among the starting materials used in the process which are useful as intermediates for the synthesis of pharmaceutical agents; and to a process for the preparation thereof.

2. Description of the Prior Art

Heretofore, as a method to remove a monoarylmethyl group, e.g., 2,4-dimethoxybenzyl, substituted at the nitrogen atom of the β-lactam ring, an oxidative cleavage using potassium persulfate has been known (J.A.C.S., 99, 2352 (1977)). However, this method has various disadvantages in yield and operation, for example, it requires a relatively high reaction temperature, it cannot be applied to unstable compounds, it requires an oxidizing agent and thus use of compounds having groups susceptible to oxidative conditions provides complicated products, and it requires reaction in a buffering solution in order to prevent the ring cleavage of the β-lactam ring and so forth.

As a result of extensive studies in pursuit of a novel process to remove a mono- or diarylmethyl group from the nitrogen atom of the β-lactam ring which is more useful, easier to handle or applicable more widely, the present inventors found that, by treating with an acid or ceric ammonium nitrate, the reaction proceeds under milder conditions than by the conventional method which employs potassium persulfate with more simplified operation and gives a desired product at a higher yield. Although several processes for producing β-lactam antibacterial substances have hitherto been known, each of these conventional processes had several drawbacks which made them infeasible for production in a large quantity. For instance, a typical process which has been used frequently comprises forming a β-lactam derivative having a nitrogen atom substituted at the α-position of the β-lactam ring by reacting an azidoacetic acid derivative with a Schiff base, but this process was not easily applied to the production on an industrial scale because the use of the azido derivative is dangerous during handling. More recently, A. K. Bose et al have proposed a process for producing a compound of the formula (A):

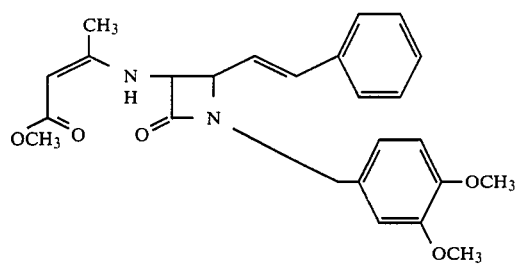

and further a process for producing bicyclic β-lactam derivatives of the formulae (B) and (C):

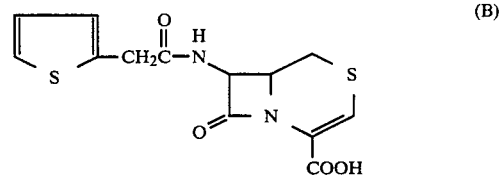

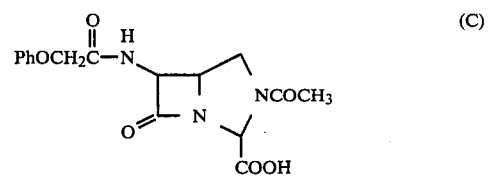

which have strong antibacterial activity and are therefore useful as medicines by converting the substituent on the nitrogen atom of the compound (A) into a hydrogen atom via several subsequent steps (Tetrahedron Letters, 2771 (1979)). The process proposed for the production of the compound (A) comprises reacting a Schiff base derived from veratrylamine and cinnamaldehyde with an (α-methyl-β-alkoxycarbonyl)-vinylaminoacetic acid in the presence of a chloroformate ester and triethylamine. However, since its reaction yield is low, and the compound (A) is obtained as an oil and is reported to be isolated and purified by a silica gel chromatography, this compound (A) and its production process still have many problems to be solved in order to be applied on a commercial scale.

Under such situations, we have conducted further studies based on the process by A. K. Bose et al. in order to obtain novel single β-lactam derivatives useful as key intermediates for producing known or novel β-lactam derivatives superior to the compound (A), by improving the above described drawbacks to make mass production feasible.

SUMMARY OF THE INVENTION

Thus, the present invention provides a process for preparing a β-lactam derivative having a hydrogen atom on the nitrogen atom of said β-lactam, which comprises reacting at β-lactam derivative having a mono- or diarylmethyl group on the nitrogen atom of the β-lactam ring with an acid or ceric ammonium nitrate to cleave the bond between the nitrogen atom and the mono- or diarylmethyl group.

The present invention also provides novel compounds having antibacterial activity, among the starting materials and the desired products obtained according to the process of the present invention, that is:

4-carboxy-3-phenylthio-3-ethyl-N-di(p-anisyl)methyl-2-azetizinone, 4-(2-carboxyethenyl)-3-phenylthio-3-ethyl-N-di(p-anisyl)methyl-2-azetizinone, 4-n-butoxycarbonyl-3-phenylthio-3-ethyl-2-azetizinone, 4-n-butoxycarbonyl-3-phenylthio-2-azetizinone, and 4-(2-acetylethenyl)-3-phenylthio-N-di(p-anisyl)-methyl-2-azetizinone.

Further, the present invention provides a process for preparing a compound represented by the formula (D):

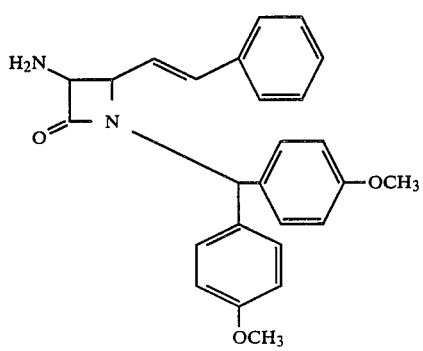
(D)

which comprises reacting an active acid anhydride derivative of the carboxylic acid compound represented by the formula (E):

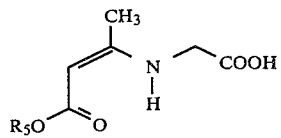
(E)

wherein R$_5$ represents a C$_1$–C$_4$ lower alkyl group such as a methyl group, an ethyl group, etc. with a Schiff base represented by the formula (F):

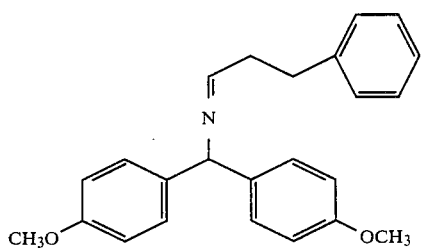
(F)

in the presence of a base to produce a β-lactam derivative represented by the formula (G):

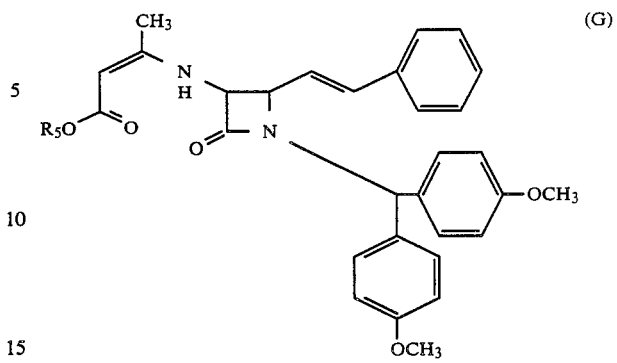
(G)

wherein R$_5$ is as defined above, and treating the resulting β-lactam derivative with an acid.

Still further, the present invention provides the key intermediates represented by the formulae (D) and (G).

DETAILED DESCRIPTION OF THE INVENTION

The process of the present invention will be described in more detail hereinbelow.

The conversion of the mono- or diarylmethyl group on the nitrogen atom of the β-lactam ring of a β-lactam derivative into a hydrogen atom can be achieved by reacting the β-lactam derivative with an acid directly or in an inert solvent, or, if necessary, in the presence of a reaction aid.

Examples of suitable acids include trifluoroacetic acid, formic acid, boron trifluoride, aluminum chloride, titanium tetrachloride, and a mixture thereof, but it is also possible to use, for example, acetic acid, trichloroacetic acid, methanesulfonic acid, benzenesulfonic acid, p-toluenesulfonic acid, stannic tetrachloride, aluminum bromide, zinc chloride, hydrogen fluoride and the like or a mixture thereof.

Examples of preferred inert solvents are trifluoroacetic acid, formic acid, acetic acid, dichloromethane, 1,2-dichloroethane, chloroform, nitromethane, and the like, or a mixture thereof, but they may be used in combination with, for example, benzene, toluene, xylene, etc.

Examples of reaction aids which can be optionally used are anisole, resorcine dimethyl ether, thioanisole, o-methoxytoluene, m-methoxytoluene, dimethyl sulfide, thiophenol, ethanethiol and the like, but preferably, anisole and resorcine dimethyl ether.

The acid is preferably used in at least an equimolar amount, and the reaction temperature is preferably below 100° C. although it is possible to retard or promote the reaction by cooling or heating as necessary. The reaction aid can be employed in an amount ranging from a trace to a large excess, preferably 1 to 6 mols per mol of the β-lactam derivative. After completion of the reaction, the resulting product can be separated by conventional techniques used in organic synthesis.

More specifically, the mono- or diarylmethyl group is suitably a methyl group substituted with one or two unsubstituted or substituted phenyl groups, such as 2,4-dimethoxybenzyl group, 2,4,6-trimethoxybenzyl group, di(4-methoxyphenyl)methyl group, 4-methoxybenzyl, phenylmethyl, diphenylmethyl, 3,4-dimethoxybenzyl, 4-dimethylaminobenzyl groups and the like, in which 2,4-dimethoxybenzyl group, 2,4,6-trimethoxybenzyl group and di(4-methoxyphenyl)methyl group are preferable.

According to the present invention, β-lactam derivatives having an unsubstituted nitrogen atom on the β-lactam ring which are excellent synthetic intermediates for the production of single β-lactam derivatives and bicyclic β-lactam derivatives useful as medicines having antibacterial activity, such as nocarbicin A, thienamycin, their analogous compounds, etc., can easily be produced from β-lactam derivatives having a mono- or diarylmethyl group as the substituent on the nitrogen atom.

Also, according to the process of this invention, the starting material, β-lactam derivative, having various substituents, e.g., a hydroxyl group, an amino group, a carboxyl group, a carboxylate group, an amido group, an alkoxy carbonylamino group, an α, β-unsaturated ester group, a carbonyl group or a protected group thereof such as its ketal, acetal or enol ester group, a halogeno atom such as chlorine, bromine, iodine and the like, a thioether group or an oxidized form thereof, i.e., a sulfone group, a nitrile group, a nitro group, an alkenyl group, etc., can be subjected to the removal of the mono- or diarylmethyl group on the nitrogen atom of the β-lactam ring to give the corresponding N-unsubstituted derivative.

In other words, the process of the present invention can be applied to a wide variety of β-lactam derivatives having a mono- or diarylmethyl group on the nitrogen atom and in accordance with the process of the present invention, a β-lactam derivative having a hydrogen atom ($R_1$ in the formula (J) below) on the nitrogen atom can be obtained from a compound represented by the formula (J):

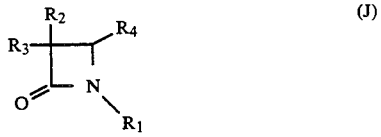

wherein $R_1$ represents a mono- or diarylmethyl group, $R_2$ represents a hydrogen atom, an arylthio group, an arylsulfonyl group, an amino group, an alkoxycarbonylamino group, an amido group or the like, $R_3$ represents a hydrogen atom or a lower alkyl group, and $R_4$ represents a carboxyl group; a lower alkoxycarbonyl group; an unsubstituted or substituted lower alkyl group wherein the substituent is a hydroxyl group, an N-lower alkanoylamino group, a halogen atom, a cyano group, a nitro group, a lower alkoxycarbonyl group, a lower alkylcarbonyl group, an arylcarbonyl group or a gem-lower alkylenedioxy group; or an unsubstituted or substituted lower alkenyl group wherein the substituent is a carboxyl group, a lower alkoxycarbonyl group, an aralkyloxycarbonyl group, a nitro group or an aryl group.

More concretely said β-lactam derivative having a mono- or diarylmethyl group on the nitrogen atom of the β-lactam ring is a compound represented by the formula:

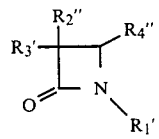

wherein $R_1'$ represents a 2,4-dimethoxybenzyl group, and a di(4-methoxyphenyl)methyl group, $R_2''$ represents a hydrogen atom, a phenylthio group, a phenylsulfonyl group, an amido group, an amino group, a lower alkoxycarbonylamino group, or 2,2,2-trichloroethoxycarbonylamino group, $R_3'$ represents a hydrogen atom, an ethyl group, and $R_4''$ represents a carboxyl group, a lower alkoxycarbonyl group; a substituted lower alkyl group wherein the substituent is a hydroxy group, an N-lower alkanoylamino group, a halogen atom, a cyano group, a nitro group, or a lower alkoxycarbonyl group; an unsubstituted or substituted lower alkenyl group wherein the substituent is an unsubstituted or substituted phenylmethyloxycarbonyl group, a lower alkoxycarbonyl group, nitro group, phenyl group, or carboxyl group.

In an alternative procedure, the conversion of the mono- or diarylmethyl group on the nitrogen atom of the β-lactam ring into a hydrogen atom can be achieved by reacting the β-lactam derivative having the mono- or diarylmethyl group substituted at the nitrogen atom of the β-lactam ring with ceric ammonium nitrate in an inert solvent.

Suitable examples of inert solvents which can be used in the above reaction are water, dimethylformamide, acetonitrile, alcohols, such as methanol, ethanol, isopropanol, etc., organic acids such as acetic acid, etc., and a mixture thereof, and these solvents can also be used in combination with tetrahydrofuran, dioxane, benzene, toluene and the like. Ceric ammonium nitrate is generally used in an amount of about 2 to 3 mols per mol of the α-lactam derivative, and the reaction temperature is preferably between 0° C. and 100° C. although the reaction can be retarded or promoted by cooling or heating. After completion of the reaction, the resulting product can be separated by conventional techniques used in the organic synthesis. Examples of the mono- or diarylmethyl group which can be subjected to the process using ceric ammonium nitrate is the same as those exemplified previously for the process using the acid.

Also, the process using ceria ammonium nitrate can be applied to the starting material, β-lactam derivative having a mono- or diarylmethyl group which is substituted with various substituents in the molecule, such as a carboxyl group or an ester group thereof, an amido group, an amino group, an alkoxycarbonylamino group, a carbonyl group, an alkenyl group, etc., whereby only the mono- or diarylmethyl group on the nitrogen atom of the β-lactam ring can be removed to produce the corresponding N-unsubstituted derivative.

As compared with the oxidation process using a persulfate, the process using ceric ammonium nitrate according to the present invention has a characteristic feature that the operation can generally be conducted at a lower temperature and is complete in a shorter time and, therefore, the process can be said to be a more advantageous process.

In accordance with the process of this invention using ceric ammonium nitrate, a β-lactam derivative having a hydrogen atom ($R_1$ in the formula (Ja) below)

on the nitrogen atom can be obtained from a compound represented by the formula (Ja):

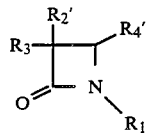
(Ja)

wherein $R_1$ and $R_3$ are as defined above, $R_2'$ represents a hydrogen atom, an arylsulfonyl group, an amino group, an alkoxycarbonylamino group or an amido group, and $R_4'$ represents a lower alkoxycarbonyl group, an unsubstituted or substituted lower alkenyl group wherein the substituent is an aryl group, an unsubstituted or substituted lower alkyl group wherein the substituent is a lower alkylcarbonyl group or an arylcarbonyl group.

More concretely the β-lactam derivative having a mono- or diarylmethyl group on the nitrogen atom of the β-lactam ring is a compound represented by the formula:

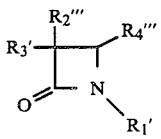

wherein $R_1'$ and $R_3'$ are as defined above, $R_2'''$ represents a hydrogen atom, a phenylsulfonyl group, an amido group, an amino group, a lower alkoxycarbonylamino group or 2,2,2-trichloroethoxycarbonylamino group, $R_4'''$ represents a lower alkoxycarbonyl group; an unsubstituted or substituted lower alkenyl group wherein the substituent is a phenyl group; a substituted lower alkyl group wherein the substituent is a lower alkylcarbonyl group or a benzoyl group.

Examples of the substituents are as follows.

$R_3$, $R_4$, $R_4'$: a lower alkyl group includes $C_1$–$C_4$ alkyl such as a methyl group, an ethyl group, an n-propyl group, an n-butyl group and the like.

$R_4$, $R_4'$: a lower alkoxycarbonyl group includes $C_1$–$C_4$ alkoxycarbonyl such as a methoxycarbonyl group, an ethoxycarbonyl group, an n-propyloxycarbonyl group, an n-butoxycarbonyl group, and the like.

$R_4$: an N-lower alkanoylamino group includes $C_2$–$C_{14}$ alkanoylamino such as an acetylamino group, a propionylamino group, and the like.

$R_4$: a lower alkylcarbonyl group includes $C_2$–$C_4$ alkylcarbonyl such as an acetyl group, a propionyl group, and the like.

$R_4$, $R_4'$: an arylcarbonyl group includes an unsubstituted or substituted benzoyl group, etc.

$R_4$: gem-lower alkylenedioxy group includes $C_2$–$C_3$ gem-alkylenedioxy such as an ethylenedioxy group and the like.

$R_4$: an aralkyloxycarbonyl group includes ar $C_1$–$C_3$ alkyloxycarbonyl such as an unsubstituted or substituted phenylmethyloxycarbonyl group, etc.

$R_4$, $R_4'$: an aryl group includes an unsubstituted or substituted phenyl group, etc.

$R_2$: an arylthio group includes an unsubstituted or substituted phenylthio group, etc.

$R_2$, $R_2'$: an arylsulfonyl group includes an unsubstituted or substituted phenylsulfonyl group, etc.

$R_2$, $R_2'$: an alkoxycarbonylamino group includes a $C_1$–$C_4$ alkoxycarbonylamino group (e.g., methoxycarbonylamino, ethoxycarbonylamino), or halo $C_1$–$C_3$ alkoxycarbonylamino group (e.g., 2,2,2-trichloroethoxycarbonylamino, etc.).

$R_2$, $R_2'$: an amido group includes an unsubstituted or substituted alkanoylamino group (e.g., acetylamino, phenoxyacetylamino, etc.), or arylcarbonylamino group, etc.

Furthermore, among the starting compounds and objective compounds described in the examples hereinbelow, the compounds represented by the formulae:

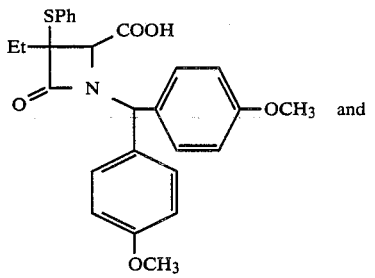
and

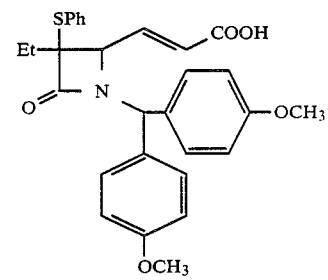

are novel compounds and have an antibacterial activity, in particular, a strong antifungal activity, and the compounds represented by the formulae:

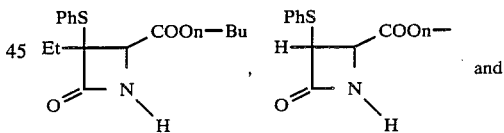
and have an antibacterial activity, in particular, a strong antibacterial activity against gram positive bacteria, and, therefore, these five compounds are particularly useful as medicines.

Still further, the present inventors found a process for preparing a β-lactam type antibacterial substance via a compound of the formula (D):

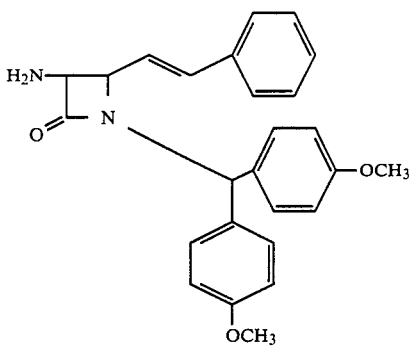

(D)

and a novel process for producing the compound (D) above.

More particularly, the compound (D) can be produced by reacting an active acid anhydride derivative of a compound represented by the formula (E):

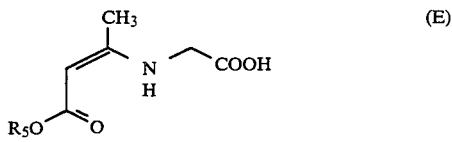

(E)

wherein $R_5$ represents a lower alkyl group such as a methyl group, an ethyl group and the like, with a Schiff base represented by the formula (F):

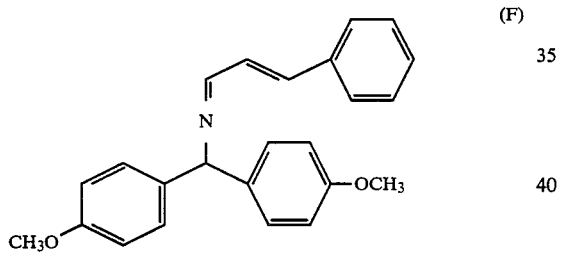

(F)

in the presence of a base in an inert solvent to produce a β-lactam derivative represented by the formula (G):

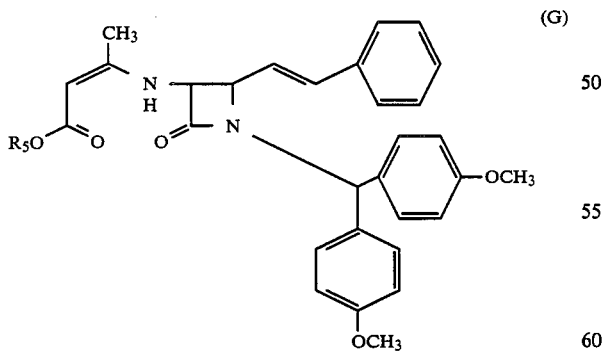

(G)

wherein $R_5$ is as defined above, and treating the resulting crystalline β-lactam derivative (G) with an acid.

While the active acid anhydride derivative of the compound (E) used in the above reaction can be produced by varius known processes, it is preferred to employ a mixed anhydride process, etc. which utilizes a chloroformate ester such as ethyl chloroformate and the like. The base is preferably triethylamine, although other various bases such as pyridine, lutidine, etc. can also be used. The inert solvent is preferably dichloromethane, but it can be used in combination with 1,2-dichloroethane, chloroform, toluene and the like.

The compound (D) can be converted into various amido derivatives represented by the formula (H) by reacting with an acylating agent such as trichloroethyl chloroformate, thienylacetyl chloride, etc. in the presence of a base as illustrated by the following reaction scheme:

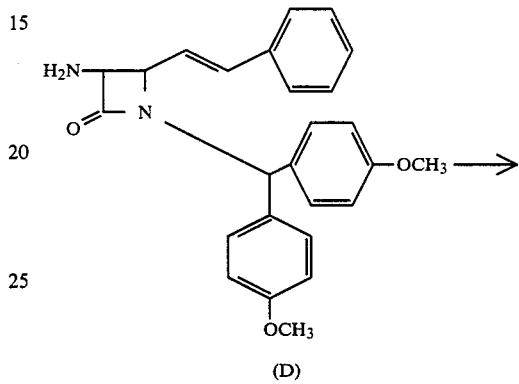

(D)

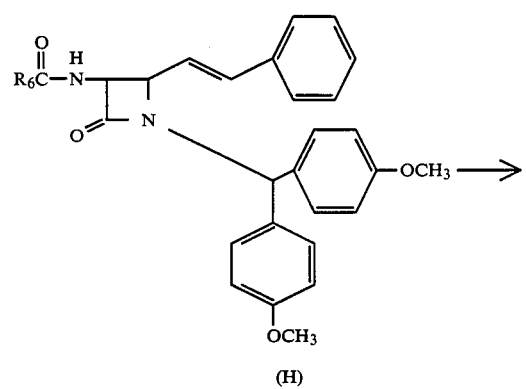

(H)

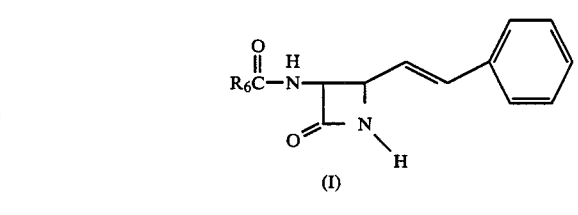

(I)

wherein $R_6$ repesents —$OCH_2CCl_3$,

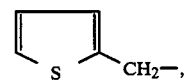

$PhOCH_2$—, $CH_3$—, etc.

Further, conversion of the di(p-anisyl)methyl group on the nitrogen atom into a hydrogen atom can easily be effected by the process of the present invention as stated above. The derivative (I) thus obtained can be converted into isocephalosporin derivative (B) and the like by processes known in the literature.

In addition to high yields in the mass production, the compounds (G) have many other advantages; for example, these compounds can be handled as crystalline compounds and therefore their isolation and purification are remarkably simplified. Furthermore, in the subsequent chemical modification steps, e.g., in the reaction for removal of the di(p-anisyl)methyl group, the reaction conditions can be generally milder than those employed in the reaction for removal of 3,4-dimethoxybenzyl group, and a higher yield of the desired compound or broader application of the process can be expected.

The starting materials, β-lactam derivatives, described in Examples hereinafter described other than the compounds (D) and (G) can be prepared by reacting an active acid anhydride of a carboxylic acid represented by the formula:

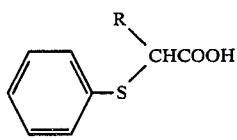

wherein R represents a hydrogen atom or an ethyl group, with a Schiff base represented by the formula:

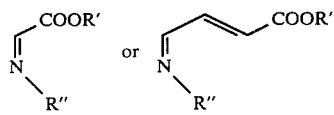

wherein R' represents a lower alkyl group or a monoarylmethyl group and R" represents a mono- or diarylmethyl group, to produce a compound represented by the formula:

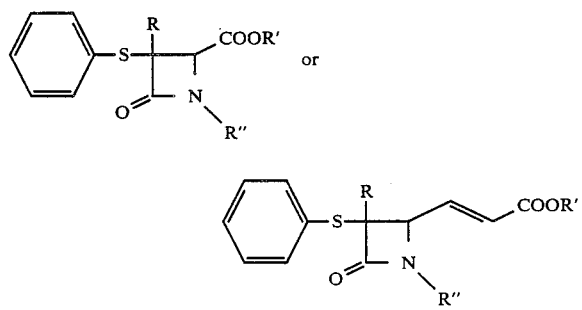

and, optionally, subjecting the resulting compound to wellknown reaction, for example, reduction, oxidation, chain extension reaction by Wittig reaction, etc., under reaction conditions which satisfy the requirements of each of these reactions to produce the desired β-lactam derivative. The preparation of these β-lactam derivatives used as starting material is illustrated in detail in Examples.

The following compounds can be prepared in the similar procedures as described in Examples 1 to 3, and 6 to 32.

4-(2-Phenylethenyl)-3-ethoxycarbonylamino-2-azetizinone 4-(2-Benzyloxycarbonylethenyl)-3-phenylthio-3-ethyl-2-azetizinone 4-(2-Ethoxycarbonylethenyl)-3-phenylthio-2-azetizinone 4-(2-Benzoylethyl)-3-phenylthio-2-azetizinone 4-n-Butoxycarbonyl-2-azetizinone The following compounds can be prepared in the similar procedures as described in Examples 4, 5, and 33 to 39.

4-(2-Phenylethenyl)-3-ethoxycarbonylamino-2-azetizinone 4-n-Butoxycarbonyl-2-azetizinone 4-Ethenyl-3-benzenesulfonyl-2-azetizinone The present invention is further illustrated in greater detail by the following Examples, but they are not to be construed as limiting the present invention. Unless otherwise indicated, all parts, percents, ratios and the like are by weight.

EXAMPLE 1

4-n-Butoxycarbonyl-3-phenylthio-3-ethyl-N-(2,4-dimethoxybenzyl)-2-azetizinone (1.2 g) obtained in Example 49 in trifluoroacetic acid (6.0 g) was stirred with boron trifluoride etherate (450 mg) and anisole (400 mg) at 40° C. for 30 minutes. Ice-water was added to the reaction mixture and extracted with ethyl acetate. The ethyl acetate extract was washed with water, aqueous sodium bicarbonate and again water, dried and evaporated to give an oil. The oil was chromatographed on silica gel to give 4-n-butoxycarbonyl-3-phenylthio-3-ethyl-2-azetizinone (79%).

IR$_{max}^{film}$ (cm$^{-1}$): 3270, 1780, 1745, 1203, 1152, 1063, 750, 690.

NMR δ (CDCl$_3$): 4.05 (1H, s), 4.17 (2H, t, J=6 Hz), 5.90 (1H, br.s).

EXAMPLE 2

4-n-Butoxycarbonyl-3-phenylthio-3-ethyl-N-di(p-anisyl)methyl-2-azetizinone (2.69 g) obtained in Example 48 in trifluoroacetic acid (20 ml) was stirred with anisole (1.34 g) at 40° C. for 5 hours and evaporated to give an oil. The oil was chromatographed on silica gel to give 4-n-butoxycarbonyl-3-phenylthio-3-ethyl-2-azetizinone (95%). This substance was identical to the compound obtained in Example 1 by the comparison of TLC, IR, and NMR.

EXAMPLE 3

4-n-Butoxycarbonyl-3-phenylthio-3-ethyl-N-di(p-anisyl)methyl-2-azetizinone (106 mg) obtained in Example 48 in dry dichloromethane (2 ml) was stirred with aluminium chloride (80 mg) at room temperature for 2 days. Water was added to the reaction mixture and the mixture was extracted with ethyl acetate. The ethyl acetate extract was washed with aqueous sodium bicarbonate and then water, dried and evaporated to give an oil. The oil was chromatographed on silica gel to give 4-n-butoxycarbonyl-3-phenylthio-3-ethyl-2-azetizinone (88%). This substance was also identical to the compound obtained in Example 1 by the comparison of TLC, IR and NMR.

EXAMPLE 4

4-n-Butoxycarbonyl-3-benzenesulfonyl-3-ethyl-N-(2,4-dimethoxybenzyl)-2-azetizinone (74 mg) obtained in Example 54 in a mixture of acetic acid and water (1:1) (2 ml) was stirred with ceric ammonium nitrate (198 mg) at 100° C. for 3 minutes, and the mixture was diluted with water and extracted with diethyl ether. The diethyl ether extract was washed with water, dried and evaporated to give an oil. The oil was chromatographed on silica gel to give 4-n-butoxycarbonyl-3-benzenesulfonyl-3-ethyl-2-azetizinone (86%).

$IR_{max}^{film}$ (cm$^{-1}$): 3300, 1782, 1742, 1210, 1145, 750, 730.

NMR δ (CDCl$_3$): 0.93 (6H, t, J=7 Hz), 2.00 (2H, q, J=7 Hz), 4.18 (2H, t, J=6 Hz), 4.75 (1H, s), 6.78 (1H, br.s).

EXAMPLE 5

4-(2-Phenylethenyl)-3-(2,2,2-trichloroethoxycarbonyl)amino-N-di(p-anisyl)methyl-2-azetizinone (59 mg) obtained in Example 43 in a mixture of dimethylformamide and water (9:1) (1.2 ml) was stirred with ceric ammonium nitrate (166 mg) at room temperature for 1 hour, and the mixture was diluted with ice-water and extracted with ethyl acetate. The ethyl acetate extract was washed with water, dried and evaporated to give an oil. The oil was chromatographed on silica gel to give 4-(2-phenylethenyl)-3-(2,2,2-trichloroethoxycarbonyl)amino-2-azetizinone (73%). m.p. 157°–161° C.

$IF_{max}^{film}$ (cm$^{-1}$): 3340, 1750, 1730, 1615, 1518, 1257, 1180, 1100, 1048, 968.

The following compounds were prepared in the similar procedures as described in Examples 1 to 3.

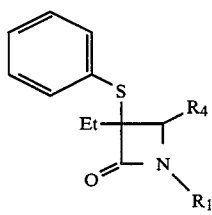

| Example No. | Starting Material | | Reaction Conditions | | Product | | | Example No. for Preparation of Starting Material |
|---|---|---|---|---|---|---|---|---|
| | R$_4$ | R$_1$ | Reagents | Temp. (Time) | R$_1$ | Yield (%) | IR, NMR, etc. | |
| 6 | —COO—n-Bu | DMB | HCOOH BF$_3$.OEt$_2$ Anisole | ~100° C. (2 hr) | H | 49 | Identical to the sample of Example 1 | 49 |
| 7 | —COO—n-Bu | DAM | CF$_3$COOH | 40° C. (6 hr) | H | 70 | Identical to the sample of Example 1 | 48 |
| 8 | —CH$_2$OH | DMB | CF$_3$COOH BF$_3$.OEt$_2$ Anisole | 40° C. (½ hr) | H | 77 | m.p. 79–81° C. $\nu_{max}^{Nujol}$: 3400, 3320, 1772, 1103, 1028 δ: 1.00 (3H, t, J=7), 1.83 (2H, q, J=7), 3.83 (2H, m) | 55 |
| 9 | —CH$_2$OH | DAM | CF$_3$COOH Anisole | 40° C. (4 hr) | H | >95 | Identical to the sample of Example 6 | 55 |
| 10 | —CH(O—)(O—) (dioxolane) | DAM | CF$_3$COOH Anisole | 40° C. (2 hr) | H | 82 | ν: 3250, 1765, 1385, 1158, 1120, 1072, 1030, 758 δ: 1.20 (3H, t, J=7), 2.07 (2H, q, J=7), 3.45 (1H, d, J=6), 3.90 (4H, br.s), 5.00 (1H, d, J=6) | 58 |
| 11 | —CH=CH—C(=O)O—CH$_2$—(p-NO$_2$-C$_6$H$_4$) | DAM | CF$_3$COOH Anisole | 38° C. (20 hr) | H | 90 | ν: 3250, 1780–1710, 1658, 1442, 1260, 1140, 1112, 985, 852, 750 δ: 1.05 (3H, t, J=7), 1.88 (2H, q, J=7), 4.28 (1H, d, J=6), 5.28 (2H, s), 6.11 (1H, d, J=16), 6.63 (1H, br.s) | 51 |
| 12 | —CH$_2$NHAc | DAM | CF$_3$COOH Anisole | 40° C. (5½ hr) | H | 81 | ν: 3300, 1758, 1640, 1265, 1188, 1072, 1000, 920 δ: 1.17 (3H, t, J=6), 1.90 (3H, s), 6.32 (1H, br.s), 6.70 (1H, br.s) | 59 |
| 13 | —(CH$_2$)$_3$OH | DMB | CF$_3$COOH BF$_3$.OEt$_2$ Anisole | 40° C. (½ hr) | H | 86 | ν: 3250, 1748, 1304, 1200, 1060, 955, 896, 750 δ: 1.15 (3H, t, J=7), 2.33 (1H, br.s), 6.47 (1H, br.s) | 61 |
| 14 | —(CH$_2$)$_3$I | DMB | CF$_3$COOH | 40° C. | H | 86 | ν: 3230, 1760, 1302, 1228, | 62 |

-continued

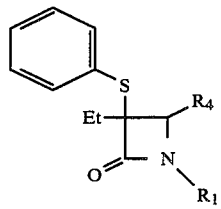

| Example No. | Starting Material R₄ | R₁ | Reaction Conditions Reagents | Temp. (Time) | Product R₁ | Yield (%) | IR, NMR, etc. | Example No. for Preparation of Starting Material |
|---|---|---|---|---|---|---|---|---|
| | | | BF₃·OEt₂ Anisole | (2 hr) | | | 1072, 1030, 920, 750 δ: 1.22 (3H, t, J=7), 3.17 (2H, m), 6.20 (1H, br.s) | |
| 15 | —CH₂Br | DAM | CF₃COOH | 40° C. (4 hr) | H | >95 | ν: 3230, 1760, 1218, 1180, 1070, 1027, 980 δ: 1.17 (3H, t, J=7), 3.37 (1H, t, J=10), 3.57 (1H, dd, J=10, J=4.5) 3.83 (1H, dd, J=10, J=4.5), 5.97 (1H, br.s) | 63 |
| 16 | —CH₂CH₂—O—C(CH₃)—O— (cyclic) | DMB | CF₃COOH BF₃·OEt₂ Anisole | 40° C. (1 hr) | H | 62 | ν: 3210, 1758, 1380, 1290, 1245, 1205, 1173, 1032, 831, 750 | 65 |
| 17 | —CH=CH—NO₂ | DAM | CF₃COOH Anisole | 40° C. (13 hr) | H | 65 | ν: 3230, 1762, 1520, 1355, 1250, 1030, 965, 923 δ: 1.13 (3H, t, J=7), 4.20 (1H, d, J=6), 5.97 (1H, br.s) | 66 |
| 18 | —COOH | DAM | CF₃COOH Anisole | 40° C. (14 hr) | H | 92 | ν: ~3200, 1745, 1310, 1210, 1160, 1045, 950, 840 δ (CD₃COCD₃): 0.97 (3H, t, J=7), 3.43 (1H, br.s), 3.83 (1H, s), 8.00 (1H, br.s) | 52 |
| 19 | —COOn-Bu | DAM | CF₃COOH, 1,3-dimethoxybenzene | 40° C. (4 hr) | H | >95 | Identical to the sample of Example 1. | 48 |
| 20 | —COOn-Bu | DMB | CF₃COOH Anisole | 72° C. (4 hr) | H | 42 | Identical to the sample of Example 1. | 49 |
| 21 | —CH=CH—COOH | DAM | CF₃COOH Anisole | 40° C. (15 hr) | H | 63 | ν: ~3200, 1755, 1650, 1175, 1025, 980, 872, 792, 745 δ (CD₃COCD₃ + D₂O): 0.97 (3H, t, J=7), 4.25 (1H, d, J=6), 6.12 (1H, d, J=16), 6.67 (1H, dd, J=16, J=6) | 53 |

-continued

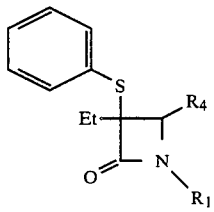

| Example No. | Starting Material R4 | R1 | Reaction Conditions Reagents | Temp. (Time) | Product R1 | Yield (%) | IR, NMR, etc. | Example No. for Preparation of Starting Material |
|---|---|---|---|---|---|---|---|---|
| 22 | —CH2—CH—NO2 (CH3) | DAM | CF3COOH Anisole | 40° C. (2 hr) | H | 98 | ν: 3250, 1765, 1545, 1390, 1362, 1190, 862<br>δ: 1.17 (3H, t, J=7), 1.53 (3H, d, J=7), 3.50 (1H, dd, J=4, J=10), 4.45 (1H, m), 5.77 (1H, br.s) | 71 |
| 23 | —CH=CH2 | DMB | CF3COOH BF3.Et2O Anisole | 40° C. (1.5 hr) | H | 87 | ν: 3240, 1740, 1505, 1432, 1240, 1170, 1018, 980, 920<br>δ: 1.07 (3H, t, J=7), 1.78 (2H, q, J=7), 3.98 (1H, d, J=6), 5.15 (1H, dd, J=1.5, J=8), 5.37 (1H, d, J=1.5), 5.75 (1H, dd, J=6, J=8) | 70 |
| 24 | —CH2—CH(CN)—COOEt | DMB | CF3COOH BF3.Et2O Anisole | 32° C. (50 min) | H | 89 | ν: 3300, 1760, 1377, 1260, 1200, 1030<br>δ: 1.32 (6H, t, J=7), 3.63 (2H, m), 4.28 (2H, q, J=7), 6.17 (1H, d, J=4.5) | 72 |

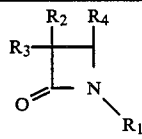

| Ex. No. | Starting Material R1 | R2 | R3 | R4 | Reaction Conditions Reagents | Temp. (Time) | Product R1 | Yield (%) | IR, NMR, etc. | Example No. for Preparation of Starting Material |
|---|---|---|---|---|---|---|---|---|---|---|
| 25 | DMB | PhSO2 | Et | COOnBu | CF3COOH BF3.Et2O Anisole | 40° C. (1.5 hr) | H | 76 | Identical to the sample of Example 4. | 54 |
| 26 | DMB | H | Et | COOnBu | CF3COOH BF3.Et2O Anisole | 40° C. (1 hr) | H | 71 | ν: 3270, 1760, 1285, 1205, 1150, 1100, 1038, 820<br>δ: 1.05 (3H, t, J = 7), 3.47 (1H, m), 4.25 (2H, q, J = 7), 6.37 (1H, br.s) | 67 |
| 27 | DAM | PhS | H | COOnBu | CF3COOH Anisole | 40° C. (10 hr) | H | 66 | ν: 3280, 1770, 1740, 1265, 1200, 1162, 1065, 990, 900, 738, 688<br>δ: 0.87 (3H, t, J = 6), 4.14 (2H, t, J = 6), 4.53 (1H, d, J = 5), 4.82 (1H, d, J = 5), 6.60 (1H, br.s) | 47 |
| 28 | DAM | PhS | H | —CH=CH2 | CF3COOH | 40° C. | H | 83 | ν: 3250, 1750, 1290, | 70 |

-continued

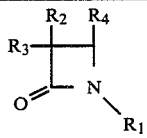

| Ex. No. | Starting Material | | | | Reaction Conditions | | Product | | | Example No. for Preparation of Starting Material |
|---|---|---|---|---|---|---|---|---|---|---|
| | $R_1$ | $R_2$ | $R_3$ | $R_4$ | Reagents | Temp. (Time) | $R_1$ | Yield (%) | IR, NMR, etc. | |
| | | | | | Anisole | (1 hr) | | | 1185, 1110, 975, 905, 817 | |
| 29 | DAM | PhS | H | -CH$_2$-CH$_2$-O=C-CH$_3$ | CF$_3$COOH, OMe-C$_6$H$_4$-OMe | R.T. (2 hr) | H | 62 | $\nu$: 3250, 1750, 1712, 1365, 1165, 1025 | 73 |
| 30 | DAM | CCl$_3$CH$_2$OCNH- (O) | H | -CH=CH-Ph | CF$_3$COOH, OMe-C$_6$H$_4$-OMe | R.T. (2 hr) | H | 54 | Identical to the sample of Example 5. | 43 |
| 31 | DAM | PhO-CH$_2$-O=C-NH | H | -CH=CH-Ph | TiCl$_4$, OMe-C$_6$H$_4$-OMe in CH$_2$Cl$_2$ | R.T. (1 d.) | H | 19 | m.p. 174–175° C. $\nu_{max}^{Nujol}$: 3270, 3210, 1770, 1725, 1672, 1242, 1225, 1082, 970 | 45 |
| 32 | DAM | H$_2$N- | H | -CH=CH-Ph | CF$_3$COOH, OMe-C$_6$H$_4$-OMe | R.T. (15 hr) | H | 29 | $\nu_{max}^{KBr}$: 3375, 1755, 1718, 1490 $\delta$ (DMSO—D$_6$): 4.21 (1H, d, J = 3), 4.22 (1H, s), 6.38 (1H, dd, J = 3, J = 15), 6.58 (1H, d, J = 15), 8.08 (1H, br.s) | 42 |

The following compounds were prepared in the similar procedures as described in Examples 4 and 5.

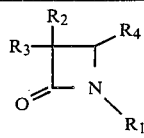

| Ex. No. | Starting Material | | | | Reaction Conditions | | Product | | | Example No. for Preparation of Starting Material |
|---|---|---|---|---|---|---|---|---|---|---|
| | $R_1$ | $R_2$ | $R_3$ | $R_4$ | Reagents | Temp. (Time) | $R_1$ | Yield (%) | IR, NMR, etc. | |
| 33 | DMB | PhSO$_2$ | Et | -CH$_2$-CH$_2$-O=C-CH$_3$ | CAN AcOH—H$_2$O (1:1) | 100° C. (1 hr) | H | 46 | $\nu$: 3320, 1750, 1715, 1305, 1210, 1142, 1070, 1017 $\delta$: 1.02 (3H, t, J = 7), 2.15 (3H, s), 2.58 (2H, t, J = 6), 3.97 (1H, m) | 73 |
| 34 | DMB | H | Et | COOnBu | CAN AcOH—H$_2$O (1:1) | 100° C. (1 hr) | H | 75 | Identical to the sample of Example 26. | 49 |

-continued

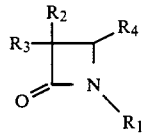

| Ex. No. | Starting Material R₁ | R₂ | R₃ | R₄ | Reaction Conditions Reagents | Temp. (Time) | Product R₁ | Yield (%) | IR, NMR, etc. | Example No. for Preparation of Starting Material |
|---|---|---|---|---|---|---|---|---|---|---|
| 35 | DAM | H | H | —CH₂—CH₂—C(=O)—Ph | CAN DMF—H₂O (9:1) | R.T. (1 hr) | H | 71 | ν: 3270, 1740, 1680, 1355, 1252, 1208, 1175 | 74 |
| 36 | DAM | (thienyl-CH₂-C(=O)-NH-) | H | —CH=CH—Ph | CAN DMF—H₂O (9:1) | R.T. (1 hr) | H | 60 | m.p. (dec) 194–200° C. $\nu_{max}^{Nujol}$: 3420, 3250, 1772, 1662, 963 | 44 |
| 37 | DAM | (PhO—CH₂—C(=O)—NH—) | H | —CH=CH—Ph | CAN DMF—H₂O (9:1) | R.T. (1 hr) | H | 72 | Identical to the sample of Example 31 | 45 |
| 38 | DAM | CH₃—C(=O)—NH | H | —CH=CH—Ph (cinnamyl) | CAN DMF—H₂O (9:1) | R.T. (1 hr) | H | 22 | m.p. 213–214° C. $\nu_{max}^{Nujol}$: 3275, 1768, 1715, 1650, 965 | 46 |
| 39 | DAM | H₂N— | H | —CH=CH—Ph | CAN DMF—H₂O (9:1) | R.T. (1.5 hr) | H | 85 | Identical to the sample of Example 32. | 42 |

(1) DMB = 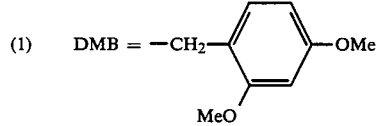

(2) DAM = 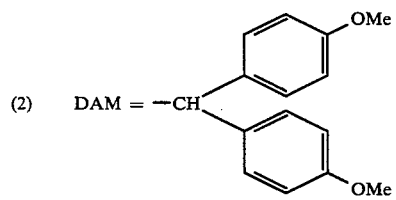

(3) ν = $IR_{max}^{film}$ (cm⁻¹), unless otherwise indicated.
(4) δ = NMR δ (CDCl₃), unless otherwise indicated.
(5) nBu, Ac and Et indicate n-butyl, acetyl and ethyl groups, respectively.
(6) CAN = ceric ammonium nitrate
(7) R.T. = room temperature

EXAMPLE 40

To N-(2-methoxycarbonyl-1-methylethenyl)glycine potassium salts (63.3 g) and triethylamine (30.3 g) in dry dichloromethane (1,250 ml) was added dropwise ethyl chloroformate (32.7 g) in dry dichloromethane (100 ml) at −20° C., and stirred for 30 minutes at the same temperature. To the reaction mixture was added dropwise transcinnamilidene-di(p-anisyl)methylamine (53.55 g) in dry dichloromethane (150 ml) at same temperature, and the reaction mixture was stood overnight at room temperature and filtered over Celite. The filtrate was washed with aqueous sodium bicarbonate (4%) and then water, dried and evaporated in vacuo to give crude crystals, which were recrystallized from diisopropyl ether to give pure crystals of 4-(2-phenylethenyl)-3-(2-methoxycarbonyl-1-methylethenyl)amino-N-di(p-anisyl)methyl-2-azetizinone (76%). m.p. 164°–166° C. $IR_{max}^{Nujol}$ (cm⁻¹): 1737, 1650, 1606, 1457, 1370, 1263, 1155, 1025, 957, 827.

The starting material, trans-cinnamilidene-di(p-anisyl)methylamine, was prepared from transcinnamaldehyde and di(p-anisyl)methylamine in the similar procedure to that described in Example 48.

EXAMPLE 41

4-(2-phenylethenyl)-3-(2-ethoxycarbonyl-1-methylethenyl)amino-N-di(p-anisyl)methyl-2-azetizinone was also prepared by using N-(2-ethoxycarbonyl-1-methylethenyl)glycine potassium salts instead of N-(2-methoxycarbonyl-1-methylethenyl)glycine potassium salts in the similar procedure to that described in Example 40. (87%). m.p. 122°–124° C.

EXAMPLE 42

To 4-(2-phenylethenyl)-3-(2-methoxycarbonyl-1-methylethenyl)amino-N-di(p-anisyl)methyl-2-azetizinone (58.7 g) in dioxane (1,174 ml) were added p-toluenesulfonic acid monohydrate (23.96 g) and water (12.4 ml) and stood overnight at room temperature. The mixture was cooled with ice-water, and precipitates were collected by filtration and dried under reduced pressure to give a white powder of 4-(2-phenylethenyl)-3-amino-N-di(p-anisyl)methyl-2-azetizinone, p-toluenesulfonic acid salts. m.p. 172°–174° C.

$IR_{max}^{Nujol}$ (cm$^{-1}$): 1760, 1610, 1508, 1460, 1373, 1245, 1175, 1030, 1003.

EXAMPLE 43

4-(2-phenylethenyl)-3-amino-N-di(p-anisyl)-methyl-2-azetizinone, prepared from the corresponding p-toluenesulfonic acid salts (5.47 g) by the usual way, in dry dichloromethane (55 ml) and triethylamine (2.83 g) were added dropwise to 2,2,2-trichloroethyl chloroformate (5.94 g) in dry dichloromethane (55 ml) at 5° C. and stirred for 10 minutes. The reaction mixture was diluted with ice-water and extracted with dichloromethane. The dichloromethane extract was washed with water, dried and evaporated in vacuo to give an oily residue, which was crystallized from methanol to give pure crystals of 4-(2-phenylethenyl)-3-(2,2,2-trichloroethoxycarbonyl)amino-N-di(p-anisyl)methyl-2-azetizinone. m.p. 189°–191° C.

$IR_{max}^{Nujol}$ (cm$^{-1}$): 3230, 1730, 1507, 1458, 1370, 1242, 1170, 1027.

EXAMPLE 44

To 4-(2-phenylethenyl)-3-amino-N-di(p-anisyl)methyl-2-azetizinone, prepared from the corresponding p-toluenesulfonic acid salts (207 mg), in dry dichloromethane (3 ml) and triethylamine (101 mg) was added dropwise 2-thienylacetyl chloride (120 mg) in dry dichloromethane (1 ml) at 5° C., followed by stirring for 1 hour. The reaction mixture was washed with water, 1N-hydrochloric acid, water, aqueous sodium bicarbonate and again water, dried and evaporated to give an oil. The oil was chromatographed on silica gel to give 4-(2-phenylethenyl)-3-(2-thienylacetyl)amino-N-di(p-anisyl)methyl-2-azetizinone.

$IR_{max}^{film}$ (cm$^{-1}$): 3270, 1740, 1650, 1245, 1177, 1030, 967, 830.

NMR δ (CDCl$_3$): 3.63 (3H, s), 3.78 (3H, s), 4.39 (1H, dd, J=5.5, J=8.0), 5.31 (1H, dd, J=5.5, J=8.0), 5.70 (1H, dd, J=8.0, J=16.5), 5.87 (1H, s), 6.24 (1H, d, J=16.5).

EXAMPLE 45

4-(2-Phenylethenyl)-3-phenoxyacetylamino-N-di(p-anisyl)methyl-2-azetizinone was prepared by using phenoxyacetyl chloride instead of 2-thienylacetyl chloride in the procedure similar to that described in Example 44.

$IR_{max}^{film}$ (cm$^{-1}$): 3300, 1745, 1672, 1508, 1490, 1243, 1170, 1030, 962, 830.

NMR δ (CDCl$_3$): 3.63 (3H, s), 3.77 (3H, s), 4.31 (2H, s), 4.42 (1H, dd, J=5 Hz, J=8 Hz), 5.40 (1H, dd, J=5 Hz, J=8 Hz), 5.85 (1H, dd, J=8 Hz, J=16 Hz), 5.97 (1H, s), 6.30 (1H, d, J=16 Hz).

EXAMPLE 46

4-(2-Phenylethenyl)-3-acetylamino-N-di(p-anisyl)-methyl-2-azetizinone was also prepared by using acetyl chloride instead of 2-thienylacetyl chloride in the procedure similar to that described in Example 44.

$IR_{max}^{film}$ (cm$^{-1}$): 3280, 1745, 1655, 1610, 1245, 1172, 1030, 965.

NMR δ (CDCl$_3$): 1.84 (3H, s), 3.64 (3H, s), 3.78 (3H, s), 4.41 (1H, dd, J=5 Hz, J=8 Hz), 5.35 (1H, dd, J=5 Hz, J=8 Hz).

The starting materials used in the examples of N-debenzylation with acids or ceric ammonium nitrate, for example, may be prepared as follows:

EXAMPLE 47

Di(p-anisyl)methylamine (20.0 g) and n-butyl glyoxylate (14.6 g) in dry toluene (1.2 l) were stirred at room temperature for 1 hour, azeotropically dehydrated with adding dry toluene, and cooled down to 65°–70° C. Triethylamine (12.4 g) and then phenylthioacetyl chloride (18.4 g) in dry toluene (83 ml) were added dropwise at 65°–70° C., followed by stirring 1 hour. The reaction mixture was washed with water, diluted hydrochloric acid, water, aqueous sodium bicarbonate, and again water, dried and evaporated in vacuo to give crude crystals, which were recrystallized from a mixture of diisopropyl ether and methanol (30:1) to give pure crystals of 4-n-butoxycarbonyl-3-phenylthio-N-di(p-anisyl)-methyl-2-azetizinone. m.p. 90°–91° C.

$IR_{max}^{film}$ (cm$^{-1}$): 1760, 1740, 1245, 1170, 1030, 820, 685.

EXAMPLE 48

Di(p-anisyl)methylamine (3.0g) and n-butyl glyoxylate (1.82 g) in dry dichloromethane (200 ml) were stirred at room temperature for 1 hour, azeotropically dehydrated with adding dry dichloromethane, and cooled with ice-water. Triethylamine (2.24 g) and then α-phenylthio-n-butyryl chloride (3.9 g) in dry dichloromethane were added dropwise at 0°–5° C., followed by stirring at 0° C. for 1 hour and then at room temperature for 2 hours. The reaction mixture was washed with water, diluted hydrochloric acid, aqueous potassium carbonate and again water, dried and evaporated to give an oil. The oil was chromatographed on silica gel to give 4-n-butoxycarbonyl-3-phenylthio-3-ethyl-N-di(p-anisyl)methyl-2-azetizinone.

$IR_{max}^{film}$ (cm$^{-1}$): 1768, 1745, 1252, 1180, 1040, 835, 760, 700.

NMR δ(CDCl$_3$): 3.72 (6H, s), 3.97 (2H, t, J=6 Hz), 5.45 (1H, s).

EXAMPLE 49

4-n-Butoxycarbonyl-3-phenylthio-3-ethyl-N-(2,4-dimethoxybenzyl)-2-azetizinone was prepared by using 2,4-dimethoxybenzylamine instead of di(p-anisyl)methylamine in the similar procedure to that described in Example 48.

$IR_{max}^{film}$ (cm$^{-1}$): 1770, 1740 (shoulder), 1290, 1210, 1155, 1035, 832, 750, 692.

NMR δ (CDCl$_3$): 0.8–2.13 (12H, m), 3.63 (3H, s), 3.80 (3H, s), 6.33 (2H, m), 6.73 (1H, d, J=8 Hz).

EXAMPLE 50

4-p-Nitrobenzyloxycarbonyl-3-phenylthio-3-ethyl-N-di(p-anisyl)methyl-2-azetizinone was prepared by using p-nitrobenzyl glyoxylate instead of n-butyl glyoxylate in the similar procedure to that described in Example 48.

IR$_{max}^{film}$ (cm$^{-1}$): 1762, 1352, 1252, 1172, 1117, 1032, 915, 860, 832, 740.

NMR δ (CDCl$_3$): 1.05 (3H, t, J=7), 3.73 (3H, s), 3.77 (3H, s), 3.90 (1H, s), 5.00 (1H, d, J=14), 5.20 (1H, d, J=14), 5.48 (1H, s).

EXAMPLE 51

4-[2-(p-nitrobenzyloxycarbonyl)ethenyl]-3-phenylthio-3-ethyl-N-di(p-anisyl)methyl-2-azetizinone was prepared by using β-p-nitrobenzyloxycarbonyl acryloaldehyde instead of n-butyl glyoxylate in the similar procedure to that described in Example 48.

IR$_{max}^{film}$ (cm$^{-1}$): 1760, 1735, 1175, 1028, 750.

NMR δ (CDCl$_3$): 0.95 (3H, t, J=7 Hz), 1.78 (2H, q, J=7 Hz), 3.75 (3H, s), 3.78 (3H, s), 4.00 (1H, d, J=9 Hz), 5.23 (2H, s), 5.77 (1H, d, J=15 Hz), 5.83 (1H, s).

The starting β-p-nitrobenzyloxycarbonyl acryloaldehyde was prepared by Wittig reaction from p-nitrobenzyl glyoxalate and formylmethylene triphenylphosphoran.

EXAMPLE 52

4-p-Nitrobenzylcarbonyl-3-phenylthio-3-ethyl-N-di(p-anisyl)methyl-2-azetizinone (2.4 g) and sodium sulfide (538 mg) in tetrahydrofuran (120 ml) and water 60 ml) were stirred at 0°-5° C. for 1 hour and then at room temperature for 3 hours, acidified with diluted hydrochloric acid and concentrated in vacuo. The residue was diluted with water and then extracted with diethyl ether. The diethyl ether layer was re-extracted with aqueous potassium carbonate and the water layer was acidified with diluted hydrochloric acid and extracted with ethyl acetate. The ethyl acetate extract was washed with water, dried and evaporated to give an oil. The oil was chromatographed on silica gel to give 4-carboxy-3-phenylthio-3-ethyl-N-di(p-anisyl)methyl-2-azetizinone.

IR$_{max}^{film}$ (cm$^{-1}$): ~2950, 1755, 1383, 1312, 1256, 1220, 1180, 1040, 838, 762.

NMR δ (CDCl$_3$): b 3.73 (3H, s), 3.77 (3H, s), 3.87 (1H, s), 5.53 (1H, s).

EXAMPLE 53

4-[2-(p-Nitrobenzyloxycarbonyl)ethenyl]-3-phenylthio-3-ethyl-N-di(p-anisyl)methyl-2-azetizinone (1.2 g) in ethanol was stirred under hydrogen atmosphere with platinum dioxide (80 mg) at room temperature for 4 hours. The catalyst was removed by filtration over Celite. The filter aid was washed with ethanol. Washings and filtrate were combined, concentrated in vacuo and diluted with diethyl ether and aqueous sodium bicarbonate. The water layer was acidified with diluted hydrochloric acid, and extracted with ethyl acetate. The ethyl acetate extract was washed with water, dried and evaporated in vacuo to give 4-(2-carboxyethenyl)-3-phenylthio-3-ethyl-N-di(p-anisyl)methyl-2-azetizinone.

IR$_{max}^{film}$ (cm$^{31}$ $^1$): ~2970, 1755, 1700, 1648, 1305, 1245, 1172, 1112, 1032, 830, 738, 695.

NMR δ (CDCl$_3$): 0.98 (3H, t, J=7 Hz), 1.88 (2H, q, J=7 Hz), 3.78 (3H, s), 3.82 (3H, s), 3.97 (1H, d, J=9 Hz), 5.72 (1H, d, J=16 Hz), 5.87 (1H, s), 8.75 (1H, br.s).

EXAMPLE 54

4-n-Butoxycarbonyl-3-phenylthio-3-ethyl-N-(2,4-dimethoxybenzyl)-2-azetizinone (1.6 g) and m-chloroperbenzoic acid (1.47 g) in chloroform (25 ml) were stirred overnight at room temperature, diluted with diethyl ether, washed with aqueous sodium bicarbonate and then water, dried and evaporated in vacuo to give 4-n-butoxycarbonyl-3-benzenesulfonyl-3-ethyl-N-(2,4-dimethoxybenzyl)-2-azetizinone.

IR$_{max}^{film}$ (cm$^{-1}$): 1775, 1745, 1210, 1152, 1033, 760.

NMR δ (CDCl$_3$): 1.00 (3H, t, J=7 Hz), 2.03 (2H, q, J=7 Hz), 3.75 (3H, s), 3.78 (3H, s), 4.12 (1H, d, J=13 Hz), 4.38 (1H, d, J=13 Hz), 6.36 (2H, m), 6.97 (1H, d, J=8 Hz).

EXAMPLE 55

4-n-Butoxycarbonyl-3-phenylthio-3ethyl-N-di(p-anisyl)methyl-2-azetizinone (4.3 g), sodium borohydride (0.93 g) and lithium iodide (3.26 g) in dry tetrahydrofuran were refluxed for 5 hours under nitrogen atmosphere, concentrated in vacuo, diluted with water, and extracted with ethyl acetate. The ethyl acetate extracted was washed with water, dried, and evaporated to give an oil. The oil was chromatographed on silica gel to give two isomers of 4-hydroxymethyl-3-phenylthio-3-ethyl-N-di(p-anisyl)methyl-2-azetizinone.

Main isomer

IR$_{max}^{film}$ (cm$^{-1}$): 3430, 1740, 1310, 1250, 1180, 1033, 830, 758.

NMR δ (CDCl$_3$): 1.20 (3H, t, J=7 Hz), 2.03 (2H, q, J=7 Hz), 3.80 (6H, s), 5.78 (1H, s).

The N-2,4-dimethoxybenzyl derivative was prepared from the corresponding ester derivative in the similar procedure as above.

IR$_{max}^{film}$ (cm$^{-1}$): 3420, 1740, 1295, 1210, 1157, 1040, 940, 838, 757.

NMR δ (CDCl$_3$): 1.13 (3H, t, J=7 Hz), 1.92 (2H, q, J=7 Hz), 2.45 (1H, br. s), 3.73 (3H, s), 3.77 (3H, s), 4.18 (2H, s), 6.37 (2H, m), 6.85 (1H, d, J=8 Hz).

EXAMPLE 56

To 4-hydroxymethyl-3-phenylthio-3-ethyl-N-di(p-anisyl)methyl-2-azetizinone (1.1 g) in dry dimethyl sulfoxide (6.4 ml) were added dropwise triethylamine (2.34 g) and then sulfur trioxide pyridine complex (1.19 g) in dry dimethyl sulfoxide (6.4 ml) at room temperature, and the mixture was stirred for 1 hour, diluted with water and extracted with diethyl ether. The diethyl ether extract was washed with water, diluted hydrochloric acid and again water, dried and evaporated in vacuo to give 4-formyl-3-phenylthio-3-ethyl-N-di(p-anisyl)methyl-2-azetizinone.

IR$_{max}^{film}$ (cm$^{-1}$): 2720, 1760, 1730, (shoulder), 1308, 1245, 1175, 1032, 830, 758.

NMR δ (CDCl$_3$): 1.10 (3H, t, J=7 Hz), 1.95 (2H, q, J=7 Hz), 3.78 (6H, s), 3.90 (1H, d, J=3 Hz), 5.73 (1H, s), 9.28 (1H, d, J=3 Hz).

The N-2,4-dimethoxybenzyl derivative was prepared from the corresponding alcohol derivative in the similar procedure as above.

IR$_{max}^{film}$ (cm$^{-1}$): 2720, 1765, 1732, 1300, 1215, 1160, 1038, 922, 840, 758.

NMR δ (CDCl$_3$): 0.93 (3H, t, J=7 Hz), 1.82 (2H, q, J=7 Hz), 3.35 (3H, s), 3.43 (3H, s), 4.33 (1H, d, J=14

Hz), 4.47 (1H, d, J=14 Hz), 6.37 (2H, m), 7.03 (1H, d, J=8 Hz), 9.37 (1H, d, J=4 Hz).

EXAMPLE 57

4-Formyl-3-phenylthio-N-di(p-anisyl)methyl-2-azetizinone was also prepared from 4-n-butoxycarbonyl-3-phenylthio-N-di(p-anisyl)methyl-2-azetizinone in the similar procedures to those described in Examples 55 and 56.

$IR_{max}^{film}$ (cm$^{-1}$): 1755, 1305, 1250, 1180, 1030, 822.

NMR δ (CDCl$_3$): 3.75 (6H, s), 3.83 (1H, d, J=3 Hz, J=4 Hz), 4.22 (1H, d, J=3 Hz), 5.85 (1H, s), 9.06 (1H, d, J=4 Hz).

EXAMPLE 58

4-Formyl-3-phenylthio-3-ethyl-N-di(p-anisyl)methyl-2-azetizinone (300 mg) and ethylene glycol in dry benzene (10 ml) were refluxed for 8 hours with azeotropically dehydrating in the presence of a catalytic amount of p-toluenesulfonic acid, washed with water, dried and evaporated in vacuo to give 4-formyl-3-phenylthio-3-ethyl-N-di(p-anisyl)methyl-2-azetizinone ethylene acetal.

$IR_{max}^{film}$ (cm$^{-1}$): 1760, 1310, 1255, 1180, 1038, 758.

NMR δ (CDCl$_3$): 1.18 (3H, t, J=7 Hz), 2.07 (2H, q, J=7 Hz), 3.55 (1H, d, J=6 Hz), 3.73 (6H, s), 4.97 (1H, d, J=6 Hz), 5.55 (1H, s).

EXAMPLE 59

To 4-formyl-3-phenylthio-3-ethyl-N-(2,4-dimethoxybenzyl)-2-azetizinone (1.488 g) and hydroxylamine hydrochloride (0.866 g) in a mixture of ethanol (18 ml) and water (6 ml) was added sodium carbonate (0.615 g), and the mixture was stirred for 4 hours at room temperature, acidified with diluted hydrochloric acid at 0°-5° C., and extracted with ethyl acetate. The ethyl acetate extract was washed with water, dried and evaporated in vacuo to give the corresponding oxime derivative. To this oxime derivative in dry benzene (10 ml) was added dropwise 1M-thionyl chloride-benzene solution (5.25 ml) with ice-cooling, and the mixture was stirred for 45 minutes at room temperature, washed with water, dried and evaporated in vacuo to give 4-cyano-3-phenylthio-3-ethyl-N-(2,4-dimethoxybenzyl)-2-azetizinone.

$IR_{max}^{film}$ (cm$^{-1}$): 2240, 1770, 1295, 1212, 1158, 1040, 940, 838. 758.

NMR δ (CDCl$_3$): 1.25 (3H, t, J=7 Hz), 2.17 (2H, q, J=7 Hz), 3.74 (3H, s), 3.80 (3H, s), 3.90 (1H, s), 4.05 (1H, d, J=14 Hz), 4.20 (1H, d, J=14 Hz), 6.30 (2H, m), 6.67 (1H, d, J=9 Hz).

To this 4-cyano derivative (380 mg) and cobaltous chloride hexahydrate (480 mg) in methanol (10 ml) was added sodium borohydride (190 ml) in some portion and the mixture was stirred for 40 minutes, diluted with water, acidified with diluted hydrochloric acid and washed with diethyl ether. The water layer was alkalized with 1N-sodium hydroxide and extracted with diethyl ether. The diethyl ether extract was washed with water, dried and evaporated in vacuo to give 4-aminomethyl-3-phenylthio-3-ethyl-N-(2,4-dimethoxybenzyl)-2-azetizinone.

$IR_{max}^{film}$ (cm$^{-1}$): 3380, 1752, 1297, 1212, 1158, 1038, 838, 758.

NMR δ (CDCl$_3$): 1.20 (3H, t, J=7 Hz), 2.85 (2H, d, J=6 Hz), 3.40 (1H, t, J=6 Hz), 3.77 (3H, s), 3.80 (3H, s), 4.17 (1H, d, J=14 Hz), 4.25 (1H, d, J=14 Hz), 6.42 (2H, m), 6.78 (1H, d, J=8 Hz).

This amino derivative (33 mg) and acetic anhydride (0.5 ml) in pyridine (0.5 ml) were stirred for 1 hour at room temperature, diluted with water, and extracted with diethyl ether. The diethyl ether extract was washed with diluted hydrochloric acid, aqueous sodium bicarbonate and water, dried and evaporated in vacuo to give 4-acetylaminomethyl-3-phenylthio-3-ethyl-N-(2,4-dimethoxybenzyl)-2-azetizinone.

$IR_{max}^{film}$ (cm$^{-1}$): 3320, 1750, 1660, 1400, 1295, 1212, 1158, 1039, 940, 839, 759.

NMR δ (CDCl$_3$): 1.20 (3H, t, J=7 Hz), 1.78 (3H, s), 3.80 (6H, s), 4.20 (2H, s), 6.45 (2H, m), 6.82 (1H, d, J=8 Hz).

EXAMPLE 60

4-n-Formyl-3-phenylthio-3-ethyl-N-(2,4-dimethoxybenzyl)-2azetizinone (1.13 g) and formylmethylene triphenylphosphoran (1.5 g) in dry benzene (25 ml) were refluxed for 6 hours and concentrated to give an oil. The oil was chromatographed on silica gel to give 4-(2-formylethenyl)-3-phenylthio-3-ethyl-N-(2,4-dimethoxybenzyl)-2azetizinone.

$IR_{max}^{film}$ (cm$^{-1}$): 2715, 1760, 1692, 1390, 1298, 1215, 1160, 1124, 1040, 839, 759.

NMR δ (CDCl$_3$): 1.08 (3H, t, J=7 Hz), 1.83 (2H, q, J=7 Hz), 3.63 (3H, s), 3.77 (3H, s), 3.98 (1H, d, J=6 Hz), 4.07 (1H, d, J=14 Hz), 4.17 (1H, d, J=14 Hz), 6.07 (1H, dd, J=16 Hz, J=6 Hz), 6.52 (1H, dd, J=16 Hz, J=7 Hz), 9.48 (1H, d, J=7 Hz).

This α,β-unsaturated aldehyde derivative (1.1 g) in ethanol (50 ml) was stirred with a palladium on charcoal (10%) catalyst under hydrogen atmosphere at room temperature. The catalyst was removed by filtration over Celite. The filter aid was washed with ethanol. Washings and filtrate were combined and evaporated in vacuo to give 4-(2-formylethyl)-3-phenylthio-3-ethyl-N-(2,4-dimethoxy-benzyl)-2-azetizinone.

$IR_{max}^{film}$ (cm$^{-1}$): 2720, 1750, 1730 (shoulder), 1400, 1298, 1212, 1158, 1123, 1038, 838, 758.

NMR δ (CDCl$_3$): 0.87 (3H, t, J=7 Hz), 1.67 (2H, q, J=7 Hz), 3,80 (6H, s), 4.10 (1H, d, J=14 Hz), 4.53 (1H, d, J=14 Hz), 9.73 (1H, br. s).

EXAMPLE 61

4-(2-Formylethyl)-3-phenylthio-3-ethyl-N-(2,4-dimethoxybenzyl)-2-azetizinone (930 mg) and sodium borohydride (128 mg) in ethanol (10 ml) were stirred for 30 minutes at room temperature, diluted with water and extracted with ethyl acetate. The ethyl acetate extract was washed with water, dried and evaporated in vacuo to give 4-(3-hydroxypropyl)-3-phenylthio-3-ethyl-N-(2,4-dimethoxybenzyl)-2-azetizinone.

$IR_{max}^{film}$ (cm$^{-1}$): 3420, 1745, 1298, 1270, 1212, 1160, 1040, 838, 758.

NMR δ (CDCl$_3$): 1.20 (3H, t, J=7 Hz), 3.67 (3H, s), 3.77 (3H, s), 4.00 (1H, d, J=15 Hz), 4.30 (1H, d, J=15 Hz), 6.30 (2H, m), 6.63 (1H, d, J=9 Hz).

EXAMPLE 62

4-(3-Hydroxypropyl)-3-phenylthio-3-ethyl-N-(2,4-dimethoxybenzyl)-2-azetizinone (207 mg) and p-toluenesulfonyl chloride (185 mg) in pyridine (2 ml) were stirred overnight with ice-cooling, diluted with water and extracted with diethyl ether. The diethyl ether extract was washed with water, diluted hydrochloric acid, aqueous sodium bicarbonate and again water, dried over anhydrous potassium carbonate and evaporated in vacuo to give the corresponding tosylate.

This tosylate and sodium iodide (300 mg) in acetone (3 ml) were refluxed for 1.5 hours, diluted with water and extracted with ethyl acetate. The ethyl acetate extract was washed with water, dried, and evaporated in vacuo to give 4-(3-iodopropyl)-3-phenylthio-3-ethyl-N-(2,4-dimethoxybenzyl)-2-azetizinone.

IR$_{max}^{film}$ (cm$^{-1}$): 1755, 1400, 1298, 1212, 1159, 1122, 1040, 838, 758.

NMR δ (CDCl$_3$): 1.23 (3H, t, J=7 Hz), 3.77 (3H, s), 3.80 (3H, s), 4.07 (1H, d, J=15 Hz), 4.30 (1H, d, J=15 Hz), 6.33 (2H, m), 6.68 (1H, d, J=8 Hz).

EXAMPLE 63

4-Bromomethyl-3-phenylthio-3-ethyl-N-di(p-anisyl)methyl-2-azetizinone was prepared from 4-hydroxymethyl-3-phenylthio-3-ethyl-N-di(p-anisyl)methyl-2-azetizinone in the procedure similar to that described in Example 62. m.p. 109°–113° C.

IR$_{max}^{Nujol}$ (cm$^{-1}$): 1750, 1362, 1255, 1177, 1038, 859, 762.

EXAMPLE 64

4-Formyl-3-phenylthio-3-ethyl-N-(2,4-dimethoxybenzyl)-2-azetizinone (1.0 g) and acetylmethylene triphenylphosphoran (1.0 g) in dry tetrahydrofuran (20 ml) were refluxed for 2.5 hours and evaporated to give an oil. The oil was chromatographed on silica gel to give 4-(2-acetylethenyl)-3-phenylthio-3-ethyl-N-(2,4-dimethoxybenzyl)-2-azetizinone.

IR$_{max}^{film}$ (cm$^{-1}$): 1760, 1677, 1360, 1292, 1256, 1210, 1157, 1038, 838, 758.

NMR δ (CDCl$_3$): 1.06 (3H, t, J=7 Hz), 1.82 (2H, q, J=7 Hz), 2.15 (3H, s), 3.65 (3H, s), 3.78 (3H, s), 3.88 (1H, d, J=7 Hz), 4.12 (2H, s), 6.05 (1H, d, J=16 Hz).

This α,β-unsaturated carbonyl derivative in ethanol (20 ml) was stirred with palladium on charcoal (10%) catalyst under hydrogen atmosphere at room temperature. The catalyst was removed by filtration over Celite. The filter aid was washed with ethanol. Washings and filtrate were combined and evaporated in vacuo to give 4-(3-oxobutyl)-3-phenylthio-3-ethyl-N-(2,4-dimethoxybenzyl)-2-azetizinone.

IR$_{max}^{film}$ (cm$^{-1}$): 1750, 1715, 1398, 1296, 1212, 1123, 1037, 835, 757.

NMR δ (CDCl$_3$): 1.23 (3H, t, J=7 Hz), 2.00 (3H, s), 3.73 (3H, s), 3.80 (3H, s), 4.03 (1H, d, J=15 Hz), 4.33 (1H, d, J=15 Hz), 6.37 (2H, m), 6.68 (1H, d, J=8 Hz).

EXAMPLE 65

4-(3-oxobutyl)-3-phenylthio-3-ethyl-N-(2,4-dimethoxybenzyl)-2-azetizinone ethylene ketal was prepared from 4-(3-oxobutyl)-3-phenylthio-3-ethyl-N-(2,4-dimethoxybenzyl)-2-azetizinone in the similar procedure to that described in Example 58.

IR$_{max}^{film}$ (cm$^{-1}$): 1760, 1265, 1212, 1158, 1122, 1038, 864, 838, 757.

NMR δ (CDCl$_3$): 1.23 (3H, t, J=7 Hz), 1.23 (3H, s), 1.98 (2H, q, J=7 Hz), 3.72 (3H, s), 3.78 (3H, s), ~3.8 (4H), 4.02 (1H, d, J=15 Hz), 4.33 (1H, d, J=15 Hz).

EXAMPLE 66

4-Formyl-3-phenylthio-3-ethyl-N-di(p-anisyl)methyl-2-azetizinone (480 mg) and nitromethane (186 mg) in dry methanol were stirred with a catalytic amount of potassium hydroxide for 3 days at room temperature, diluted with water and extracted with ethyl acetate. The ethyl acetate extract was washed with water, dried and evaporated to give an oil. The oil was chromatographed on silica gel to give 4-(2-nitro-1-hydroxyethyl)-3-phenylthio-3-ethyl-N-di(p-anisyl)methyl-2-azetizinone.

IR$_{max}^{film}$ (cm$^{-1}$): 3400, 1750, 1522, 1180, 1032, 830, 758.

NMR δ (CDCl$_3$): 1.33 (3H, t, J=7 Hz), 3.53 (1H, d, J=9 Hz), 3.76 (3H, s), 3.80 (3H, s).

This alcohol derivative (44 mg) and methanesulfonyl chloride (13.2 mg) in dry dichloromethane were stirred with triethylamine (34 mg) at 0° C. for 4 hours, washed with water, diluted hydrochloric acid and again water, dried and evaporated in vacuo to give 4-(2-nitroethenyl)-3-phenylthio-3-ethyl-N-di(p-anisyl)methyl-2-azetizinone.

IR$_{max}^{film}$ (cm$^{-1}$): 1760, 1520, 1170, 1114, 1030, 955, 830, 758.

NMR δ (CDCl$_3$): 1.47 (3H, t, J=7 Hz), 1.97 (2H, q, J=7 Hz), 3.77 (6H, s), 4.00 (1H, d, J=8 Hz), 5.73 (1H, s), 6.57 (1H, d, J=12 Hz), 6.80 (1H, dd, J=12 Hz, J=8 Hz).

EXAMPLE 67

4-n-Butoxycarbonyl-3-phenylthio-3-ethyl-N-(2,4-dimethoxybenzyl)-2-azetizinone (100 mg) in ethanol (5 ml) was refluxed with an excess of Raney nickel catalyst for 12 hours. The catalyst was removed by filtration. The filter aid was washed with ethanol. Washings and filtrate were combined and evaporated in vacuo to give 4-n-butoxycarbonyl-3-ethyl-N-(2,4-dimethoxybenzyl)-2-azetizinone.

IR$_{max}^{film}$ (cm$^{-1}$): 1760, 1740 (shoulder), 1295, 1212, 1158, 1035, 838.

NMR δ (CDCl$_3$): 3.75 (3H, s), 3.78 (3H, s), 3.97 (1H, d, J=6 Hz), 4.10 (1H, d, J=6 Hz), 4.13 (1H, d, J=15 Hz), 4.60 (1H, d, J=15 Hz), 6.43 (2H, m), 7.10 (1H, d, J=8 Hz).

EXAMPLE 68

4-n-Butoxycarbonyl-N-di(p-anisyl)methyl-2-azetizinone was prepared from 4-n-butoxycarbonyl-3-phenylthio-N-di(p-anisyl)methyl-2-azetizinone in the procedure similar to that described in Example 67.

IR$_{max}^{film}$ (cm$^{-1}$): 1770, 1740, 1305, 1250, 1175, 1035, 825.

NMR δ (CDCl$_3$): 0.73–1.73 (7H, m), 2.96 (1H, dd, J=3.6 Hz, J=15 Hz), 3.12 (1H, dd, J=5.5 Hz, J=15 Hz), 3.77 (6H, s), 3.95 (1H, dd, J=3.6 Hz, J=5.5 Hz), 5.83 (1H, s).

EXAMPLE 69

4-Formyl-N-di(p-anisyl)methyl-2-azetizinone was also prepared from 4-n-butoxycarbonyl-N-di(p-anisyl)methyl-2-azetizinone in the similar procedures to those described in Examples 55 and 56.

IR$_{max}^{film}$ (cm$^{-1}$): 1750, 1720 (shoulder), 1305, 1180, 1110, 1035, 960, 827, 817.

NMR δ (CDCl$_3$): 3.76 (6H, s), 5.99 (1H, s), 9.07 (1H, d, J=5.5 Hz).

EXAMPLE 70

To 4-formyl-3-phenylthio-3-ethyl-N-(2,4-dimethoxybenzyl)-2-azetizinone (615 mg) and methyltriphenylphosphonium bromide (785 mg) in dry dichloromethane (25 ml) was added dropwise aqueous sodium hydroxide (50%) (25 ml) at room temperature, stirred vigorously for 15 minutes and neutralized with 1M-oxalic acid solution. The dichloromethane layer was washed with water, dried and evaporated to give an oil.

The oil was chromatographed on silica gel to give 4-ethenyl-3-phenylthio-3-ethyl-N-(2,4-dimethoxybenzyl)-2-azetizinone.

IR$_{max}^{film}$ (cm$^{-1}$): 1750, 1390, 1285, 1210, 1152, 1030, 990, 935, 835, 690.

NMR δ (CDCl$_3$): 1.07 (3H, t, J=7.5 Hz), 1.82 (2H, m), 3.67 (3H, s), 3.77 (3H, s), 3.95 (1H, d, J=15 Hz), 4.32 (1H, d, J=15 Hz), 5.23 (2H, m), 5.70 (1H, m), 6.33 (2H, m), 6.74 (1H, d, J=9 Hz).

4-Ethenyl-3-phenylthio-N-di(p-anisyl)methyl-2-azetizinone was prepared from 4-formyl-3-phenylthio-N-di(p-anisyl)methyl-2-azetizinone and methyltriphenylphosphonium bromide in the similar procedure to that above.

IR$_{max}^{film}$ (cm$^{-1}$): 1755, 1305, 1250, 1175, 1110, 1030, 935, 820.

NMR δ (CDCl$_3$): 3.73 (6H, s), 4.00 (1H, d, J=3 Hz), 5.05 (2H, m), 5.59 (1H, s), 5.60 (1H, m).

EXAMPLE 71

To 4-(2-nitro-1-propenyl)-3-phenylthio-3-ethyl-N-di(p-anisyl)methyl-2-azetizinone (645 mg), which was derived from 4-formyl-3-phenylthio-3-ethyl-N-di(p-anisyl)methyl-2-azetizinone and nitroethane in the similar procedure to that described in Example 66, in dry methanol (9 ml) was added sodium borohydride (47.5 mg) with ice-cooling, stirred for 3.5 hours at room temperature, diluted with ethyl acetate, washed with water, dried and evaporated to give an oil. The oil was chromatographed on silica gel to give 4-(2-nitropropyl)-3-phenylthio-3-ethyl-N-di(p-anisyl)methyl-2-azetizinone.

IR$_{max}^{film}$ (cm$^{-1}$): 1750, 1560, 1500, 1168, 1110, 1025.

NMR δ (CDCl$_3$): 1.23 (3H, t, J=7 Hz), 1.37 (3H, d, J=7 Hz), 3.80 (6H, s), 5.70 (1H, s).

EXAMPLE 72

4-Formyl-3-phenylthio-3-ethyl-N-(2,4-dimethoxybenzyl)-2-azetizinone (1.0 g) and ethyl cyanoacetate (440 mg) in dry ethanol (20 ml) were refluxed with a catalytic amount of potassium hydroxide for 15 hours. After cooling, sodium borohydride (30 mg) was added to the reaction mixture at −5° to 0° C., stirred for 20 minutes, diluted with ice-water and extracted with ethyl acetate. The ethyl acetate extract was washed with water, dried and then evaporated to give an oil. The oil was chromatographed on silica gel to give 4-(2-cyano-2-ethoxycarbonylethyl)-3-phenylthio-3-ethyl-N-(2,4-dimethoxybenzyl)-2-azetizinone.

IR$_{max}^{film}$ (cm$^{-1}$): 2240, 1755, 1297, 1265, 1210, 1168, 1032, 940, 835.

NMR δ (CDCl$_3$): 1.30 (3H, t, J=7 Hz), 3.77 (3H, s), 3.83 (3H, s), 4.27 (2H, q, J=8 Hz).

EXAMPLE 73

The following compounds were prepared in the similar procedures to those described in Reference Examples 55, 56 and 64.

| Starting Materials | Products | |
|---|---|---|
| 4-n-Butoxycarbonyl-3-phenylthio-N—di(p-anisyl)methyl-2-azetizinone | 4-(3-Oxobutyl)-3-phenylthio-N—di(p-anisyl)methyl-2-azetizinone | ν: 1755, 1713, 1305, 1250, 1175, 1112, 1032, 825<br>δ: 2.00 (3H, s), 2.23 (2H, t, J=7), 3.30 (1H, dd, J=3, J=4), 3.40 (1H, dd, J=3, J=4), 3.77 (6H, s), 3.83 (1H, d, J=3), 5.67 (1H, s) |
| 4-n-Butoxycarbonyl-3-benzenesulfonyl-3-ethyl-N—(2,4-dimethoxybenzyl)-2-azetizinone | 4-(3-Oxobutyl)-3-benzenesulfonyl-3-ethyl-N—(2,4-dimethoxybenzyl)-2-azetizinone | ν: 1760, 1715, 1305, 1207, 1145, 1080, 1035, 938, 835<br>δ: 1.03 (3H, t, J=7), 2.11 (3H, s), 3.79 (6H, s), 6.40 (2H, m), 7.02 (1H, d, J=9) |

EXAMPLE 74

4-(2-Benzoylethyl)-N-di(p-anisyl)methyl-2-azetizinone was prepared from 4-formyl-N-di(p-anisyl)methyl-2-azetizinone and benzoylmethylene triphenylphosphoran in the similar procedure to that described in Example 64.

IR$_{max}^{film}$ (cm$^{-1}$): 1740, 1678, 1508, 1243, 1174, 1105, 1028, 807.

NMR δ (CDCl$_3$): 1.83 (2H, q, J=7 Hz), 2.60–3.30 (4H), 3.75 (3H, s), 3.81 (3H, s), 5.74 (1H, s).

While the invention has been described in detail and with reference to specific embodiments thereof, it will be apparent to one skilled in the art that various changes and modifications can be made therein without departing from the spirit and scope thereof.

What is claimed is:

1. A process for preparing a β-lactam derivative of the formula:

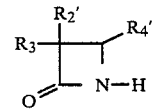

wherein R$_2'$ represents a hydrogen atom, an arylthio group, an arylsulfonyl group, an amino group, a lower alkoxycarbonylamino group, a haloalkoxycarbonylamino group or an amido group, R$_3$ represents a hydrogen atom or a lower alkyl group, and R$_4'$ represents a carboxyl group; a lower alkoxycarbonyl group; an unsubstituted or substituted lower alkyl group wherein the substituent is a hydroxy group, an N-lower alkanoylamino group, a halogen atom, a cyano group, a nitro group, a lower alkoxycarbonyl group, a lower alkylcarbonyl group, an arylcarbonyl group or a gem-lower alkylenedioxy group or an unsubstituted or substituted lower alkenyl group wherein the substituent is a carboxyl group, a lower alkoxycarbonyl group, an aralkyloxycarbonyl group, a nitro group or an aryl group, which process comprises reacting a β-lactam derivative of the formula

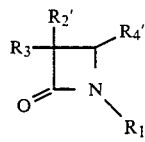

wherein R₁ represents a mono- or diarylmethyl group and R₂', R₃ and R₄' are as defined above, with ceric ammonium nitrate having the formula Ce(NO₃)₆(NH₄)₂ to cleave the bond between the nitrogen atom on said β-lactam ring and the mono- or diarylmethyl group represented by R₁.

2. The process according to claim 1, wherein said mono- or diarylmethyl group is a 2,4-dimethoxybenzyl group, a 2,4,6-trimethoxybenzyl group, a di(4-methoxyphenyl)methyl group, a 4-methoxybenzyl group, a phenylmethyl group, a diphenylmethyl group, a 3,4-dimethoxybenzyl group or a 4-dimethylaminobenzyl group.

3. The process according to claim 1, wherein said mono- or diarylmethyl group is a 2,4-dimethoxybenzyl group or a di(4-methoxyphenyl)methyl group.

4. The process according to claim 1, wherein said β-lactam derivative having a mono- or diarylmethyl group on the nitrogen atom of the β-lactam ring is a compound represented by the formula

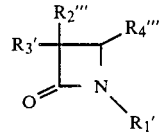

wherein R₁' represents a 2,4-dimethoxybenzyl group or a di(4-methoxyphenyl)methyl group, R₃' represents a hydrogen atom or an ethyl group, R₂''' represents a hydrogen atom, a phenylsulfonyl group, an amido group, an amino group, a lower alkoxycarbonylamino group or a 2,2,2-trichloroethoxycarbonylamino group, and R₄''' represents a lower alkoxycarbonyl group; an unsubstituted or substituted lower alkenyl group wherein the substituent is a phenyl group; a substituted lower alkyl group wherein the substituent is a lower alkylcarbonyl group or a benzoyl group.

* * * * *